United States Patent
Jung et al.

(10) Patent No.: US 12,274,768 B2
(45) Date of Patent: Apr. 15, 2025

(54) CLEANER BASE, CLEANING COMPOSITION INCLUDING THE SAME, AND METHOD OF PREPARING THE CLEANING COMPOSITION

(71) Applicant: AMOREPACIFIC CORPORATION, Seoul (KR)

(72) Inventors: Chang Jo Jung, Yongin-si (KR); Gooyoung Kwon, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 366 days.

(21) Appl. No.: 17/828,113

(22) Filed: May 31, 2022

(65) Prior Publication Data

US 2023/0099108 A1 Mar. 30, 2023

(30) Foreign Application Priority Data

Sep. 24, 2021 (KR) .......... 10-2021-0126583

(51) Int. Cl.
| | | |
|---|---|---|
| *A61K 8/00* | (2006.01) | |
| *A61K 8/02* | (2006.01) | |
| *A61K 8/04* | (2006.01) | |
| *A61K 8/41* | (2006.01) | |
| *A61K 8/42* | (2006.01) | |
| *A61K 8/46* | (2006.01) | |
| *A61K 8/73* | (2006.01) | |
| *A61K 8/81* | (2006.01) | |
| *A61Q 5/02* | (2006.01) | |

(52) U.S. Cl.
CPC .............. *A61K 8/022* (2013.01); *A61K 8/042* (2013.01); *A61K 8/416* (2013.01); *A61K 8/42* (2013.01); *A61K 8/466* (2013.01); *A61K 8/731* (2013.01); *A61K 8/732* (2013.01); *A61K 8/737* (2013.01); *A61K 8/8152* (2013.01); *A61Q 5/02* (2013.01)

(58) Field of Classification Search
None
See application file for complete search history.

(56) References Cited

U.S. PATENT DOCUMENTS

| | | | |
|---|---|---|---|
| 2016/0060578 A1 | 3/2016 | Klinkhammer et al. | |
| 2018/0243192 A1* | 8/2018 | Hwang | A61K 8/81 |
| 2020/0405587 A1 | 12/2020 | Song et al. | |
| 2021/0002586 A1* | 1/2021 | Anderson | C11D 3/40 |
| 2024/0041707 A1* | 2/2024 | Morvan | A61K 8/44 |

FOREIGN PATENT DOCUMENTS

| | | |
|---|---|---|
| CN | 113201415 A | 8/2021 |
| JP | 4488818 B2 | 6/2010 |
| JP | 2015-074762 A | 4/2015 |
| JP | 2015-083591 A | 4/2015 |
| JP | 5914961 B2 | 5/2016 |
| KR | 10-2018-0068522 A | 6/2018 |
| KR | 10-1965607 B1 | 4/2019 |
| KR | 10-2020-0019701 A | 2/2020 |
| KR | 10-2020-0021096 A | 2/2020 |
| KR | 10-2020-0128545 A | 11/2020 |
| KR | 10-2227345 B1 | 3/2021 |
| WO | 97/45510 A1 | 12/1997 |
| WO | 2009/153311 A2 | 12/2009 |
| WO | 2010/090354 A1 | 8/2010 |

OTHER PUBLICATIONS

Carbonated shampoo / Damaged wool shampoo / Volume shampoo "Boris the Pick GRANULE Powder shampoo", https://blog.naver.com/uniqueplace_/222309039434, Apr. 13, 2021, 31 total pages (retrieved May 3, 2022).

"Mildly acidic foam cleanser for oily skin Sababian face powder: Naver blog", https://blog.naver.com/iamchocolat/221965825234, 2020, 41 total pages (retrieved May 3, 2022).

Extended European Search Report issued Feb. 3, 2023 in European Application No. 22194181.8.

* cited by examiner

*Primary Examiner* — Necholus Ogden, Jr.
(74) *Attorney, Agent, or Firm* — Sughrue Mion, PLLC

(57) ABSTRACT

Provided are a cleaner base containing a solid composition including a solid surfactant and a water-soluble polymer, a gel cleaning composition having a viscosity of greater than or equal to about 50 cPs including the cleaner base containing a solid composition and water, and a method for preparing the gel cleaning composition.

9 Claims, No Drawings

CLEANER BASE, CLEANING COMPOSITION INCLUDING THE SAME, AND METHOD OF PREPARING THE CLEANING COMPOSITION

CROSS-REFERENCE TO RELATED APPLICATION

This application claims priority to and the benefit of Korean Patent Application No. 10-2021-0126583 filed in the Korean Intellectual Property Office on Sep. 24, 2021, the entire contents of which are incorporated herein by reference.

BACKGROUND OF THE INVENTION

(a) Field of the Invention

The present disclosure relates to a cleaner base, a cleaning composition including the cleaner base and water and having a viscosity of greater than or equal to about 50 cPs, and a method for preparing the cleaning composition.

(b) Description of the Related Art

Skin is a part of a body directly exposed to an external environment and thus does not only serve as a protective film protecting important organs of the body but also regulates moisture evaporation and protects the body from external infections. However, the skin may block penetration of viruses from the outside but when exposed to excessive UV rays, pollutants, or the like, skin irritations and inflammatory reactions such as erythema, edema, itching, and the like are caused. Accordingly, keeping the skin clean is important not only for the skin but also for the whole body. In general, a cosmetic composition for human body cleaning includes ingredients such as surfactants, thickeners, skin conditioning agents, hair conditioning agents, oils, preservatives, fragrances, water, and the like, wherein particularly, the surfactants realize a cleaning effect of the human skin including scalp, hair, and the like and thus are of high importance. Recently, due to plastic pollution, efforts to not use plastic containers by developing recyclable or biodegradable containers in cosmetics or household products or using solid detergents such as soap and the like are being made. However, these efforts may result in cost burden or cause inconvenience due to inferior usability compared with existing gel-type products used by customers. Accordingly, since a composition for human body cleaning may be easily prepared in a method of mixing a solid composition and water without the plastic containers, but efforts to improve usability of the composition for a human body without deteriorating foam quality, compared with a conventional composition for human body cleaning, are being made, there is a growing trend of consumers who are willing to choose a composition for human body cleaning that emphasizes eco-friendliness, as long as it keeps equivalent cleaning power or foam quality to the conventional products.

SUMMARY OF THE INVENTION

An embodiment provides a cleaner base containing a solid composition that does not require a plastic container and is environmentally friendly, and can provide a cleaning composition having excellent foam quality and feeling of use.

Another embodiment provides a gel-type cleaning composition having a viscosity of greater than or equal to about 50 cPs, including the cleaner base containing the solid composition and water.

Another embodiment provides a method for preparing a gel-type cleaning composition having a viscosity of greater than or equal to about 50 cPs, which includes adding water to the cleaner base containing the solid composition.

According to an embodiment, a cleaner base containing a solid composition including a solid surfactant and a water-soluble polymer is provided.

The solid composition may be a powder type.

The solid surfactant may include an anionic surfactant, an amphoteric surfactant, a nonionic surfactant, or a combination thereof.

The solid surfactant may include an anionic surfactant and an amphoteric surfactant.

The solid surfactant may include an anionic surfactant and a nonionic surfactant.

The solid surfactant may include an amphoteric surfactant and a nonionic surfactant.

The anionic surfactant may include at least one anionic surfactant, for example one or more types of anionic surfactants, the amphoteric surfactant may include at least one amphoteric surfactant, for example one or more types of amphoteric surfactants, and the nonionic surfactant may include at least one nonionic surfactant, for example one or more types of nonionic surfactants.

The anionic surfactant may include at least one, for example two types selected from a sulfate-based anionic surfactant, a sulfonate-based anionic surfactant, a glutamate-based anionic surfactant, a glycinate-based anionic surfactant, a taurate-based anionic surfactant, an alaninate-based anionic surfactant, a sulfosuccinate-based anionic surfactant, a carboxylate-based anionic surfactant, a phosphate-based anionic surfactant, or a sarcosinate-based anionic surfactant. The amphoteric surfactant may be at least one, for example two types selected from a betaine-based surfactant, a sultaine-based (sulfobetaine-based) amphoteric surfactant, or a propionate-based amphoteric surfactant. The nonionic surfactant may include at least one, for example two types selected from an amide-based nonionic surfactant, an amine oxide-based nonionic surfactant, a fatty alcohol nonionic surfactant, or a fatty acid nonionic surfactant.

The anionic surfactant may include a glutamate-based anionic surfactant and a sulfosuccinate-based anionic surfactant.

The glutamate-based anionic surfactant may be included in an amount of greater than that of the sulfosuccinate-based anionic surfactant.

The sulfosuccinate-based anionic surfactant may be included in an amount of about 30 parts by weight to about 50 parts by weight based on 100 parts by weight of the glutamate-based anionic surfactant.

The water-soluble polymer may include a polysaccharide, a gum, an acrylic polymer, a polyquaternium-based polymer, a guar-based polymer, or a combination thereof.

The polysaccharide may include a phosphate-based polymer.

The gum may include a xanthan gum, a tamarind seed gum, or a combination thereof.

The acrylic polymers may include ammonium acryloyl dimethyl taurate/VP copolymer.

The polyquaternium-based polymer may include polyquaternium-10.

The guar-based polymer may include guarhydroxypropyltriammonium chloride.

The solid surfactant may be included in an amount equal to or greater than that of the water-soluble polymer.

The solid surfactant and the water-soluble polymer may be included in a weight ratio of about 1:1 to about 14:1.

The gum may be a tamarind seed gum, and the solid surfactant and the tamarind seed gum may be included in a weight ratio of about 1:1 to about 7:1.

The cleaner base may be a cleaner base for preparing a gel-type cleaning composition having a viscosity of greater than or equal to about 50 cPs.

According to another embodiment, a gel-type cleaning composition having a viscosity of greater than or equal to about 50 cPs, including the cleaner base containing the solid composition, and water, is provided.

The water may be included in an amount equal to or greater than that of the cleaner base.

Another embodiment provides a method for preparing a gel-type cleaning composition having a viscosity of greater than or equal to about 50 cPs, including adding water to the cleaner base containing the solid composition.

The solid composition in the cleaner base according to an embodiment serves as a highly concentrated solid powder cleaner base, and when it is mixed with a certain amount of water and diluted, it has a viscosity above a certain level, so that a gel-type cleaning composition with excellent ease of use may be prepared directly.

DETAILED DESCRIPTION OF THE EMBODIMENTS

Hereinafter, exemplary embodiments of the present disclosure will be described in detail, and may be easily performed by a person having ordinary skill in the related art. However, this disclosure may be embodied in many different forms and is not construed as limited to the example embodiments set forth herein.

As used herein, when specific definition is not otherwise provided, "combination" refers to mixing or copolymerization.

Hereinafter, a cleaner base containing a solid composition according to an embodiment is described.

Recently, due to environmental pollution of plastics, efforts to not use plastic containers by developing containers to be recyclable or biodegradable in cosmetics or household products or using solid cleaners such as soaps and the like are being made. However, these efforts may result in a cost burden or bring about inconvenience due to inferior usability to a gel-type cleaner used by existing customers.

Accordingly, the present inventors have repeated research in various ways to provide an eco-friendly and easy-to-use cleaner that meets the recent issues as described above and as a result, found that when a solid surfactant and a water-soluble polymer are used to prepare a solid composition, the solid composition is easily thickened just through a mixing process with water, so that anyone may prepare a gel composition, completing the present invention.

Specifically, the cleaner base containing a solid composition according to an embodiment, for example, a highly concentrated powder-type formulation is diluted in water to prepare a gel-type cleaner in an existing container used by consumers, which may maintain usability and quality but use no plastic container at all. The existing container is classified into an one-touch type, a pump type, a tube type, a jar type, etc., and the cleaner base containing the solid composition according to an embodiment may be placed in the existing container, and then water is just added thereto to prepare the gel-type cleaner, wherein the solid composition is controlled with respect to a composition so that the prepared gel-type cleaning composition may have, for example, viscosity of greater than or equal to about 50 cPs at room temperature (about 25° C.). When the cleaning composition has viscosity of less than about 50 cPs, the feeling of use is greatly deteriorated, which is not suitable.

A solid composition included in a cleaner base according to an embodiment includes a solid surfactant and a water-soluble polymer.

For example, the solid composition may be a powder type, but is not limited thereto, and may be a tablet type, a jelly type, etc. as well as the powder type.

For example, the solid surfactant may include an anionic surfactant, an amphoteric surfactant, a nonionic surfactant, or a combination thereof.

The solid surfactant may include an anionic surfactant and an amphoteric surfactant.

The solid surfactant may include an anionic surfactant and a nonionic surfactant.

The solid surfactant may include an amphoteric surfactant and a nonionic surfactant.

The solid surfactant may include one or more types of anionic surfactants, one or more types of amphoteric surfactants, one or more types of nonionic surfactants, or a combination thereof.

For example, the anionic surfactant may include a sulfate-based surfactant, a sulfonate-based surfactant, a glutamate-based surfactant, a glycinate-based surfactant, a taurate-based surfactant, an alaninate-based surfactant, a sulfosuccinate-based surfactant, a carboxylate-based surfactant, a phosphate-based surfactant, a sarcosinate-based surfactant, and the like, but is not limited thereto, and the anionic surfactant may be in a form of a solid powder.

In addition, it may further include an amphoteric surfactant, a nonionic surfactant, or a combination thereof as an auxiliary surfactant together with the anionic surfactant. The amphoteric surfactant may include a betaine-based surfactant, a sultaine-based (sulfobetaine-based) surfactant, a propionate-based surfactant, etc. and the nonionic surfactant may include an amide-based surfactant, an amine oxide-based surfactant, a fatty alcohol surfactant, a fatty acid surfactant, etc., but the present disclosure is not limited thereto.

The amphoteric surfactant and the nonionic surfactant may also be in a form of a solid powder.

For example, the solid surfactant may include one or more, for example two or more, for example two types of anionic surfactants. Herein, the two types of anionic surfactants may be a glutamate-based anionic surfactant and a sulfosuccinate-based anionic surfactant.

For example, the glutamate-based anionic surfactant may be included in an amount of greater than that of the sulfosuccinate-based anionic surfactant. Specifically, the sulfosuccinate-based anionic surfactant may be included in an amount of about 30 parts by weight to about 50 parts by weight based on 100 parts by weight of the glutamate-based anionic surfactant. When the glutamate-based anionic surfactant and the sulfosuccinate-based anionic surfactant are used in the same contents as above, when the cleaner base containing the solid composition according to an embodiment is mixed with water, viscosity may be easily controlled to be greater than or equal to about 50 cPs at room temperature.

For example, the water-soluble polymer may be a water-soluble thickening polymer that may be easily thickened by diluting the water-soluble polymer in water, for example, by mixing by hand or shaking in a container, but not by a mechanical force and specifically, may include polysaccharide, gum, an acrylic polymer, a polyquaternium-based polymer, a guar-based polymer, or a combination thereof.

For example, the polysaccharide may include a cellulose-based polymer, a phosphate-based polymer, or a combination thereof. Specifically, the polysaccharide may include a phosphate-based polymer, for example hydroxypropyl starch phosphate, but is not limited thereto.

For example, the gum may include a xanthan gum, a gellan gum, a tamarind seed gum, or a combination thereof. Specifically, the gum may include a xanthan gum, a tamarind seed gum, or a combination thereof, but is not necessarily limited thereto.

For example, the acrylic polymer may include an ammonium acryloyl dimethyl taurate/VP copolymer, but is not necessarily limited thereto.

For example, the polyquaternium-based polymer may include polyquaternium-10, but is not necessarily limited thereto.

For example, the guar-based polymer may include guar-hydroxypropyltriammonium chloride, but is not necessarily limited thereto. For example, the solid surfactant may be included in an amount equal to or greater than that of the water-soluble polymer. Specifically, the solid surfactant and the water-soluble polymer may be included in a weight ratio of about 1:1 to about 14:1. When the solid surfactant and the water-soluble polymer are included in the same amounts as above, viscosity at room temperature may be easily controlled to be greater than or equal to about 50 cPs, when the solid composition in a cleaner base according to an embodiment is mixed with water.

For example, the gum is tamarind seed gum, wherein the solid surfactant and the tamarind seed gum may be included in a weight ratio of about 1:1 to about 7:1. When the gum is the tamarind seed gum, and the solid surfactant is included at 7 times more than that of the tamarind seed gum, viscosity at room temperature may be lowered to less than about 50 cPs, which is undesirable.

On the other hand, the solid composition itself may be a highly concentrated solid powder cleaner base. Particularly, the cleaner base according to an embodiment is mixed with water to prepare a gel-type cleaning composition (or a cleaner) that can be stored for a long time, which clearly differs from a conventional powder-type cleaner, that is, a cleaner of directly using foam created by putting powder in hands and mixing it with water. While the conventional powder-type cleaner forms bubbles when mixed with water, it has to be immediately used but cannot be stored for a long time, but the cleaner base according to an embodiment is just mixed with water to easily prepare a gel-type cleaner, and in addition, the gel-type cleaner has to be contained in a foaming pump container to create foam and thus can be stored for a long time when once easily made by a user, which are completely different from the conventional powder-type cleaner.

For example, the cleaner base may be a cleaner base for preparing a gel-type cleaning composition (or cleaner) having a viscosity of greater than or equal to about 50 cPs.

Another embodiment provides a cleaning composition having a viscosity of greater than or equal to about 50 cPs, including the cleaner base containing the solid composition and water.

The cleaning composition necessarily has viscosity of greater than or equal to about 50 cPs, wherein the viscosity is viscosity at room temperature (about 25° C.). When the cleaning composition has viscosity in the above range, a gel-type composition may be formed through thickening. It is very important that the cleaning composition has viscosity within the range, because excellent foam quality or feeling of use is secured, only when the gel-type composition is formed.

For example, the cleaning composition may have a viscosity of greater than or equal to about 80 cPs, for example greater than or equal to about 500 cPs, for example greater than or equal to about 1000 cPs, for example greater than or equal to about 2000 cPs, for example greater than or equal to about 3000 cPs, for example greater than or equal to about 4000 cPs, for example, greater than or equal to about 5000 cPs, or for example greater than or equal to about 6000 cPs, at room temperature (25° C.), but the present disclosure is not necessarily limited thereto.

For example, the cleaning composition may have a viscosity of less than or equal to about 500000 cPs, for example less than or equal to about 450000 cPs, for example less than or equal to about 400000 cPs, for example less than or equal to about 350000 cPs, or for example less than or equal to about 300000 cPs at room temperature (25° C.), but the present disclosure is not necessarily limited thereto.

For example, the cleaning composition may be a gel type.

For example, the water may be included in an amount of equal to or greater than that of the cleaner base containing the solid composition. Specifically, the cleaner base containing the solid composition and the water may be included in a weight ratio of about 1:9 to about 5:5 but is not limited thereto, and as long as foam quality and feeling of use are maximized by appropriately controlling the viscosity at room temperature of the gel-type cleaning composition, the solid composition and water may be included in any weight ratio.

In addition, another embodiment provides a method of preparing a cleaning composition with viscosity of greater than or equal to about 50 cPs, which includes adding water to the cleaner base containing the solid composition.

Herein, the cleaning composition may be a gel type, and the water and the cleaner base containing the solid composition may be mixed within the same content range as above.

Since the method of preparing the cleaning composition is just adding water to the cleaner base containing the solid composition, which a consumer alone may very easily perform without buying an unnecessary plastic container for using the cleaning composition, the more the solid composition according to an embodiment and a cleaning composition including the same are used according to this preparing method, the less plastic is naturally used, and accordingly, the solid composition according to an embodiment and the cleaning composition including the same are very environmentally-friendly.

Hereinafter, the present invention will be described in more detail through examples and comparative examples. These examples are provided only for understanding the present invention, but the scope of the present invention is not limited to these examples and experimental examples, and modifications, substitutions, and insertions commonly known in the art may be performed. They may be included in the scope of the present invention.

Preparation of Cleaner Base

Cleaner bases were prepared to have each composition shown in Table 1.

TABLE 1

(unit: g)

| | Components | Prep. Ex. 1 | Prep. Ex. 2 | Prep. Ex. 3 | Prep. Ex. 4 | Prep. Ex. 5 | Prep. Ex. 6 | Prep. Ex. 7 | Prep. Ex. 8 | Prep. Ex. 9 | Prep. Ex. 10 | Prep. Ex. 11 |
|---|---|---|---|---|---|---|---|---|---|---|---|---|
| Surfactant | Sodium lauroyl glutamate | 5 | 5 | 5 | 5 | 5 | 5 | 5 | 5 | 5 | 5 | 5 |
| | Disodium lauryl sulfosuccinate | 2 | 2 | 2 | 2 | 2 | 2 | 2 | 2 | 2 | 2 | 2 |
| Polymer Polysaccharide | Hydroxy ethyl cellulose | 1 | — | — | — | — | — | — | — | — | — | — |
| | Hydroxypropyl starch phosphate | — | 7 | — | — | — | — | — | — | — | — | — |
| Gum | Xanthan gum | — | — | 1 | — | — | — | — | — | — | — | — |
| | Gellan gum | — | — | — | 1 | — | — | — | — | — | — | — |
| | Tamarind seed gum | — | — | — | — | 3 | — | — | — | — | 1 | 0.5 |
| Acrylic | Carbomer | — | — | — | — | — | 1 | — | — | — | — | — |
| | Ammoniumacryloyldimethyltaurate/VP copolymer | — | — | — | — | — | — | 3 | — | — | — | — |
| Polyquaternium-based | polyquaternium-10 | — | — | — | — | — | — | — | 1 | — | — | — |
| Guar-based | Guarhydroxypropyl triammonium chloride | — | — | — | — | — | — | — | — | 1 | — | — |

Preparation of Cleaning Composition 1

Each cleaner base according to Preparation Examples 1 to 11 and water were mixed in a weight ratio of 1:9 to prepare cleaning compositions, and the cleaning compositions were measured with respect to viscosity at 25° C. by using a Brookfield viscometer LV (No. 3 spindle, 12 rpm) and also, examined regarding whether or not the solid compositions were respectively separated (stability) in the aqueous solutions with the naked eye, and the results are shown in Table 2.

TABLE 2

| | Prep. Ex. 1 | Prep. Ex. 2 | Prep. Ex. 3 | Prep. Ex. 4 | Prep. Ex. 5 | Prep. Ex. 6 | Prep. Ex. 7 | Prep. Ex. 8 | Prep. Ex. 9 | Prep. Ex. 10 | Prep. Ex. 11 |
|---|---|---|---|---|---|---|---|---|---|---|---|
| Viscosity (cPs) | — (Viscosity is unmeasurable) | 11700 | 6130 | — (Viscosity is unmeasurable) | 7270 | — (Viscosity is unmeasurable) | 6290 | 2100 | 980 | 85 | 15 |
| Stability | separated | stable | stable | separated | stable | separated | stable | stable | separated | stable | stable |

Preparation of Cleaning Composition 2

Compared with the cleaning compositions according to Preparation Examples 2, 3, 5, and 8, the cleaning compositions according to Preparation Examples 2-1, 3-1, 5-1, and 8-1 were prepared by mixing each cleaner base and water in a weight ratio of 3:7 instead of 1:9 and then, measured with respect to viscosity at 25° C. by using a Brookfield viscometer LV (No. 3 spindle, 12 rpm) and also, checked regarding whether or not the cleaner bases were separated (stability) in the aqueous solutions with the naked eye, and the results are shown in Table 3.

TABLE 3

|  | Prep. Ex. 2-1 | Prep. Ex. 3-1 | Prep. Ex. 5-1 | Prep. Ex. 8-1 |
|---|---|---|---|---|
| Viscosity (cPs) | 520 | 7500 | 15250 | 8100 |
| Stability | stable | stable | stable | stable |

Evaluation 1: Foam Quality

Ryo Jay Yang Yoon-mo shampoo (Amorepacific) and the cleaning compositions according to Preparation Examples 2, 2-1, 3, 3-1, 5, 5-1, 8, 8-1, 10, and 11 were evaluated with respect to foam quality, and the results are shown in Table 4. Specifically, shampoo bubble evaluation comparison of the cleaning compositions was conducted through a human hair tress by asking 10 female panels aged 25 to 40 years to give 9 to the best and 1 to the worst and thus evaluate bubble volumes and bubble elasticity.

TABLE 4

|  | Ryo Jay Yang Yoon-mo shampoo | Prep. Ex. 2 | Prep. Ex. 3 | Prep. Ex. 5 | Prep. Ex. 8 | Prep. Ex. 2-1 | Prep. Ex. 3-1 | Prep. Ex. 5-1 | Prep. Ex. 8-1 | Prep. Ex. 10 | Prep. Ex. 11 |
|---|---|---|---|---|---|---|---|---|---|---|---|
| Bubble volume | 5 | 6 | 6 | 4 | 5 | 6 | 4 | 6 | 5 | 5 | 3 |
| Bubble elasticity | 5 | 7 | 8 | 5 | 5 | 5 | 8 | 7 | 6 | 4 | 2 |

Referring to Table 4, when the cleaning compositions had viscosity of less than 50 cPs at 25° C., foam quality was deteriorated, and furthermore, the cleaning compositions according to an embodiment exhibited equal to or higher foam quality than that of a conventional gel-type cleaning composition.

Evaluation 2: Feeling of Use According to Viscosity

The panels participated in Evaluation 1 were asked to take an appropriate amount of each cleaning composition according to Preparation Examples 5, 5-1, 10, and 11 on hands or tools for use on hair or skin and to evaluate feeling of use as suitable or unsuitable. The results are shown in Table 5.

TABLE 5

|  | Prep. Ex. 5 | Prep. Ex. 5-1 | Prep. Ex. 10 | Prep. Ex. 11 |
|---|---|---|---|---|
| Viscosity (cPs) | 7270 | 15250 | 85 | 15 |
| Feeling of use | suitable | suitable | suitable | unsuitable |

Referring to Table 5, when the cleaning composition had viscosity of less than 50 cPs at 25° C., the cleaning composition was difficult to take on hands or tools.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

What is claimed is:

1. A solid cleaner base composition, comprising a solid surfactant and a water-soluble polymer,
    wherein the solid surfactant comprises an anionic surfactant, an amphoteric surfactant, a nonionic surfactant, or a combination thereof,
    wherein the water-soluble polymer consists of a tamarind seed gum,
    wherein the solid surfactant and the tamarind seed gum are included in a weight ratio of about 1:1 to about 7:1, and
    wherein the solid cleaner base composition is a cleaner base for preparing a gel cleaning composition having a viscosity of greater than or equal to about 50 cPs.

2. The solid cleaner base composition of claim 1, wherein the solid cleaner base composition is a powder.

3. The solid cleaner base composition of claim 1, wherein the anionic surfactant is at least one selected from a sulfate-based anionic surfactant, a sulfonate-based anionic surfactant, a glutamate-based anionic surfactant, a glycinate-based anionic surfactant, a taurate-based anionic surfactant, an alaninate-based anionic surfactant, a sulfosuccinate-based anionic surfactant, a carboxylate-based anionic surfactant, a phosphate-based anionic surfactant, or a sarcosinate-based anionic surfactant, the amphoteric surfactant is at least one selected from a betaine-based amphoteric surfactant, a sultaine-based amphoteric surfactant, sulfobetaine-based amphoteric surfactant, or a propynoate-based amphoteric surfactant, and the nonionic surfactant is at least one selected from an amide-based nonionic surfactant, an amine oxide-based nonionic surfactant, a fatty alcohol nonionic surfactant, or a fatty acid nonionic surfactant.

4. The solid cleaner base composition of claim 3, wherein the anionic surfactant includes a glutamate-based anionic surfactant and a sulfosuccinate-based anionic surfactant.

5. The solid cleaner base composition of claim 4, wherein the glutamate-based anionic surfactant is included in an amount of greater than that of the sulfosuccinate-based anionic surfactant.

6. A gel cleaning composition having a viscosity of greater than or equal to about 50 cPs, comprising the solid cleaner base composition of claim 1 and water.

7. The gel cleaning composition of claim 6, wherein the water is included in an amount of equal to or greater than that of the solid cleaner base composition.

8. A method for preparing a gel cleaning composition having a viscosity of greater than or equal to about 50 cPs, comprising adding water to the solid cleaner base composition of claim 1.

9. The method of claim 8, wherein the water is included in an amount equal to or greater than that of the solid cleaner base composition.

* * * * *